United States Patent [19]

Wright

[11] Patent Number: 4,742,156
[45] Date of Patent: * May 3, 1988

[54] PEPTIDE ANTAGONISTS OF NEUROKININ B AND OPTHALMIC SOLUTIONS CONTAINING THEM

[75] Inventor: David E. Wright, Ambler, Pa.

[73] Assignee: McNeilab, Inc., Fort Washington, Pa.

[*] Notice: The portion of the term of this patent subsequent to May 12, 2004 has been disclaimed.

[21] Appl. No.: 902,351

[22] Filed: Aug. 29, 1986

Related U.S. Application Data

[63] Continuation-in-part of Ser. No. 781,839, Sep. 30, 1985, Pat. No. 4,665,157.

[51] Int. Cl.$^4$ ..................... A61K 37/02; C07C 103/52
[52] U.S. Cl. .................................................... 530/328
[58] Field of Search ........................... 530/328; 514/15

[56] References Cited

U.S. PATENT DOCUMENTS 4,481,139 11/1984 Folkers et al. ..................... 530/327
4,481,190 11/1984 Nestor et al. ......................... 514/16
4,665,157 5/1987 Wright ................................ 530/328

OTHER PUBLICATIONS

Vaught et al., "Tachykinin-Like Central Activity of Neuromedin K in Mice", European Journal of Pharmacology, 103 (1984) pp. 355-357.
Kangawa et al., "Neuromedin K: A Novel Mammalion Tachykinin Identified in Porcine Spinal Cord", Biochem. Biophys. Res. Comm., vol. 114, No. 2, 1983, pp. 533-540.
Society for Neuroscience Abstracts, vol. 10, Part 1, 14th Annual Meeting, Oct. 10-15, 1984, Anaheim, CA, No. 63.1, "Multiple Tachykinin Receptors: Substance P . . . ", Wright et al., p. 211.
Ninth American Peptide Symposium, Abstracts, U. of Toronto, Jun. 23-28, 1985, P-WTh-114, "Tachykinin Antagonists and Multiple Receptors", Wright et al.
"A Substance P Antagonist . . . ", Science, vol. 214, Nov. 27, 1981, G. Holmdahl et al., pp. 1029-1031.
"Long-Term Administration of a Substance P Antagonist . . . ", Experientia 40 (1984), Birkhauser Verlag, Switzerland, G. Bynke et al., pp. 368-369.
Munekata et al., "Neurokinin α and β, Synthesis and Pharmacological Properties", Chemistry Letters, pp. 1013-1016, 1984.
Vaught et al., "A Characterization of Kyotorphin (Tyr-Arg)-Induced Antinociception", European Journal of Pharmacology, 79 (1982) pp. 167-173.

*Primary Examiner*—Delbert R. Phillips
*Assistant Examiner*—Nathan M. Nutter
*Attorney, Agent, or Firm*—David J. Levy

[57] ABSTRACT

Four decapeptides found to be analgesics and have antagonist activity to Neurokinin B which is also known as Neuromedin K. The decapeptide are of the following formula (I):

$$A^1\text{-D-Pro}^2\text{His}^3\text{-D}^4\text{Phe}^5\text{D-Trp}^6\text{Val}^7\text{-D-Trp}^8\text{-Leu}^9\text{-Nle}^{10}\text{-NH}_2 \qquad (I)$$

wherein $A^1$ and $D^4$ are Asp or D-Asp amino acids. Also described is an opthalmic solution to treat pain or inflammation and an HPLC separation method using piperidine.

10 Claims, No Drawings

PEPTIDE ANTAGONISTS OF NEUROKININ B AND OPTHALMIC SOLUTIONS CONTAINING THEM

The present application is a continuation-in-part of U.S. Ser. No. 781,839 filed Sept. 30, 1985, now U.S. Pat. No. 4,665,157.

BACKGROUND OF THE INVENTION

Peptide antagonists of substance P and of LHRH are described in U.S. Pat. Nos. 4,481,139 and 4,481,190, respectively. Antagonists of Substance P have been shown to be useful as opthalmic anti-inflammatory agents as described by G. Holmdahl et al. in Science, Vol. 214, pages 1029–1031 (Nov. 27, 1981) and by G. Bynke et al. in Experientia, 40, pages 368–369 (1984).

Neurokinin B, also known as $\beta$-neurokinin and neuromedin K, recently has been isolated from porcine spinal cord; Kimura, s., et al, Proc. Jap. Acad. Ser. B, 59:101 (1983) and Kangawa, K., et al., Biochem. Biophys. Res. Comm., 114:533 (1983). This decapeptide has the following formula: $Asp^1$-$Met^2$-$His^3$-$Asp^4$-$Phe^5$-$Phe^6$-$Val^7$-$Gly^8$-$Leu^9$-$Met^{10}$-$NH_2$. This decapeptide has the same C-terminal sequence shared by all tachykinins, but its N-terminal region is strikingly different especially when compared to that of substance P. Neurokinin B has two aspartic acid residues (a negatively charged peptide) while substance P has an arginine and lysine residue (positive charges) in this region. Antagonists to substance P have been developed as reviewed by Regoli, D., et al., Pharmacology 28:301 (1984). As yet no antagonists of Neurokinin B have been described. The substitution of D-Pro for $Pro^2$ and $Phe^7$ and $Gly^9$ by D-Trp results in an antagonist of substance P which has analgesic properties; Akerman, B., et al., Acta Physio. Scand. 114:631 (1982). Neurokinin B has different biological properties from substance P which may be representative of the large difference in the N-terminal region of these two peptides; Vaught, J. L., et al., Europ. J. Pharmacol. 103:355 (1984); Munekata, E., et al., Chem. Lett., 1013 (1984).

SUMMARY OF THE INVENTION

The present invention comprises novel, highly potent decapeptide analogs of Neurokinin B which have $His^3$-$Phe^5$-$Val^7$-$Leu^9$ as does Neurokinin B, but have substitutions at positions 1, 2, 4, 6, 8, 10. These substitutions have resulted in potent antagonists of Neurokinin B and Substance P which also are long acting analgesic and anti-inflammatory agents. Compounds of the invention are of the following formula (I):

$A^1$-D-$Pro^2$-$His^3$-$D^4$-$Phe^5$-D-$Trp^6$-$Val^7$-D-$Trp^8$-$Leu^9$-$Nle^{10}$-$NH_2$ wherein
$A^1$ is $Asp^1$ or D-$Asp^1$; and
$D^4$ is $Asp^4$ or D-$Asp^4$,
and the pharmaceutically acceptable salts, e.g. acid-addition salts such as the trifluoroacetate, acetate and hydrochloride and base-addition salts such as the sodium and pyridine salts.

DETAILED DESCRIPTION OF THE INVENTION

The polypeptides of the present invention may be synthesized by any techniques that are known to those skilled in the peptide art, a summary of which can be found in J. Stewart and J. D. Young, Solid Phase Peptide Synthesis, Pierce Chemical Co., Rockford, IL, 1984.

As an example as to how peptides of the invention were synthesized, the following experimental procedure is described. The protected amino acids were purchased from Bachem, Torrance, Calif. Alpha amino functions were protected by the Boc-group. Side chain functions were protected by the benzyl group for aspartic acid and the dinitrophenyl group for histidine.

The peptides were constructed by the stepwise solid-phase method on a 4-methylbenzhydrylamine resin. In the reaction vessel of a Beckman 990 Peptide Synthesizer was placed 5.0 g (2 mmoles) of 4-methylbenzhydrylamine resin. Amino acids were added sequentially to this resin by means of the following synthesis program.

| Step | Description | Times | Duration (minutes) |
|---|---|---|---|
| 1 | $CH_2Cl_2$ Wash | 1 | 1.0 |
| 2 | 50% $CF_3CO_2H$/46% $CH_2Cl_2$/ 2% anisole/2% m-cresol-Deprotection | 1 | 2.0 |
| 3 | 50% $CF_3CO_2H$/46% $CH_2Cl_2$/ 2% Anisole/2% m-cresol-Deprotection | 1 | 20 |
| 4 | $CH_2Cl_2$ Wash | 4 | 1.0 |
| 5 | 10% diisopropylethylamine/ $CH_2Cl_2$ | 2 | 2.0 |
| 6 | $CH_2Cl_2$ Wash | 3 | 1.0 |
| 7 | $N^\alpha$—Boc-Amino Acid Solution | 1 | 1.0 |
| 8 | N,N'—dicyclohexylcarbodiimide solution (coupling reaction) | 1 | 70 |
| 9 | $CH_2Cl_2$ Wash | 2 | 1.0 |
| 10 | Isopropanol Wash | 1 | 1.0 |
| 11 | Dimethylformamide Wash | 1 | 1.0 |
| 12 | 10% Diisopropylethylamine/ $CH_2Cl_2$ Wash | 1 | 1.0 |
| 13 | $CH_2Cl_2$ Wash | 2 | 1.0 |
| 14 | $N^\alpha$—Boc-amino acid solution | 1 | 1.0 |
| 15 | N,N'—Dicyclohexylcarbodiimide (coupling reaction) | 1 | 70 |
| 16 | $CH_2Cl_2$ Wash | 2 | 1.0 |
| 17 | Isopropanol Wash | 1 | 1.0 |
| 18 | Dimethylformamide Wash | 1 | 1.0 |
| 19 | $CH_2Cl_2$ Wash | 2 | 1.0 |

Steps 1–19 complete a coupling cycle for one amino acid and completeness of the coupling reaction is checked by the ninhydrin method of E. Kaiser, et al., Anal. Biochem., 34:595 (1970) and periodically by amino acid analysis.

The resin was coupled sequentially with a 3–5 molar excess of each protected amino acid and DCC for each coupling. If after two couplings an amino acid was not completely coupled to the growing peptide chain, a third coupling of that amino acid was employed. If the third coupling failed to achieve the desired results, the peptide chain was terminated by treatment with acetic anhydride, specifically a treatment of (1) 3% acetic anhydride ($CH_2Cl_2$, 1 time, 40 min); (2) $CH_2Cl_2$ (wash, 4 times, 1.0 min); (3) isopropanol (wash, 2 times, 1.0 min); (4) $CH_2Cl_2$ (wash, 4 times, 1.0 min).

After the last amino acid was incorporated into the peptide, the N-terminal Boc-group was removed with trifluoroacetic acid/$CH_2Cl_2$ as described above. Next the peptide resin was washed with $CH_2Cl_2$, isopropanol, $CH_2Cl_2$ and dried.

To remove the dinitrophenyl group, the peptide resin (5 g) was placed in 40 ml dimethylformamide followed by 2 ml thiophenol. The mixture was stirred for 2 hr at room temperature after which time the peptide-resin was filtered and washed with DMF (3 times), isopropanol (3 times) and CH$_2$Cl$_2$ (3 times). The peptide-resin was then dried.

The peptide was cleaved from the resin using trifluoromethanesulfonic acid. The peptide-resin (4.5 g) was placed in 50 ml trifluoroacetic acid along with 0.8 ml thioanisole and 1.6 ml trifluoromethanesulfonic acid. The mixture was stirred under argon for 2 hr at room temperature after which time the contents were filtered, and the cleaved resin was washed with trifluoroacetic acid (15 ml, 3 times). The filtrate was concentrated to an oil by evaporation using nitrogen, and the resulting oil was cooled to 5° C. and dissolved in 50% acetic acid. The acetic acid solution was passed through a 10 g column of Bio-Rad AG1-X2 resin, and fractions were collected. Those fractions which were ninhydrin positive were pooled and concentrated to dryness in vacuo. The resulting residue was taken-up in 50% acetic acid and was applied to a SP-Sephadex (7 g) column previously washed with 1N HCl, H$_2$O, 1M pyridine (aqueous), H$_2$O and acetic acid. Elution started with 50% acetic acid (~400 ml) and was followed by a linear gradient of 0 to 0.3M pyridine in 50% acetic acid (total amount used—400 ml) with another 200 ml 0.3M pyridine in 50% acetic acid finally being passed through the column. The compound of interest elutes at the end of the 0 to 0.3M pyridine gradient. The fractions which incude the desired peptide were concentrated in vacuo, redissolved in 50% acetic acid and lyophilized. This ion-exchange chromatography step was repeated in the same manner as described above on the desired isolated fraction. Final purification was achieved by semi-preparative HPLC using either TMS, C-8, CN OR phenyl columns. The peptide fraction of interest was dissolved in a minimum amount of acetic acid/acetonitrile/0.1% trifluoroacetic acid and an acetonitrile gradient of 10% to 40% (10 min and hold) was used employing 0.1% TFA as the aqueous solvent. Ultraviolet detection was used at 305 nm. At least two semi-preparative HPLC runs were required to obtain around 150 mg pure (>95% peptide). All peptides were analyzed for purity at each stage of the purification by analytical HPLC using a Zorbax ® 3 micron C-8 (6.2 mm×8 cm) column and an acetonitrile gradient of 20% to 50% in 3 min and hold. The aqueous solvent was 0.1% trifluoroacetic acid and detection was at 280 nm. A new purification HPLC method not hither to described for peptide purification also was developed. In this case, a Hamilton PRP-1 column (305 mm×7.0 mm), supplied by Hamilton Co. of Reno. Nev. 89502, was used along with a basic volatile buffer. Specifically, the peptide of interest was dissolved in a minimum amount of piperidine, H$_2$O, acetonitrile and was applied to the column. The gradient was 10% to 40% with respect to acetonitrile (holding to 40%) with the aqueous solvent being 0.1% piperidine. Improved solubility of the peptide and improved separations using this basic HPLC semi-preparative system was seen. The desired peptide was identified by amino acid analysis and fast atom bombardment mass spectroscopy.

EXAMPLES 1-4

Using the above techniques, the following decapeptides were synthesized:

Example 1

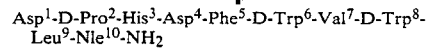
Asp$^1$-D-Pro$^2$-His$^3$-Asp$^4$-Phe$^5$-D-Trp$^6$-Val$^7$-D-Trp$^8$-Leu$^9$-Nle$^{10}$-NH$_2$

Example 2

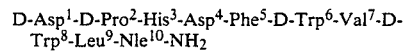
D-Asp$^1$-D-Pro$^2$-His$^3$-Asp$^4$-Phe$^5$-D-Trp$^6$-Val$^7$-D-Trp$^8$-Leu$^9$-Nle$^{10}$-NH$_2$

Example 3

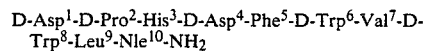
D-Asp$^1$-D-Pro$^2$-His$^3$-D-Asp$^4$-Phe$^5$-D-Trp$^6$-Val$^7$-D-Trp$^8$-Leu$^9$-Nle$^{10}$-NH$_2$

Example 4

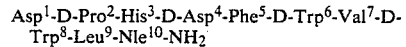
Asp$^1$-D-Pro$^2$-His$^3$-D-Asp$^4$-Phe$^5$-D-Trp$^6$-Val$^7$-D-Trp$^8$-Leu$^9$-Nle$^{10}$-NH$_2$ Inhibition of Tachykinin-Induced Scratching The tachykinin-induced mouse scratching assay was used to evaluate the ability of the Neurokinin B analogs of the invention to act in vivo as antagonists. This test was chosen since scratching is well documented to be a reproducible, characteristic central effect of tachykinin agonists which can be blocked by tachykinin antagonists, see Hylden and Wilcox, Brain Res. 217:212 (1981); Piercey et al., Science 214:1361, (1981); Vaught et al., Eur. Journal Pharmacol. 103:355, (1984).

Male, Swiss CD-1 mice (Charles River, Kingston, NY) weighing between 18–24 g were used in all experiments. They were allowed food and water ad libitum and each animal was used only once. Substance P, Neurokinin B, bombesin (a compound which induces scratching but is not a tachykinin), [D-Pro$^2$, D-Trp$^{7,9}$]-Substance P$_{(1-11)}$ and the product of Example 1 were dissolved in 0.01N acetic acid. The products of Examples 2, 3 and 4 were dissolved in 0.1N NaOH; DMSO and H$_2$O (1:1:4.7 v/v). These vehicles, injected intrathecally to mice, produced no overt behavioral effects.

To determine the activity of substance P, Neurokinin B and bombesin, these agonists were injected intrathecally (max. volume 5 ml) according to the method of Hylden et al. described in Eur. Journal Pharmacol. 67:313 (1980). Following the intrathecal injection of agonist, the animals were placed into individual plexiglass observation chambers and observed for five min for the occurrence of the characteristic reciprocal hindlimb scratching response (caudally directed scratching of the body interchangeably by the hind limbs). Animals were scored as either responders or non-responders. In order to assess the ability and specificity of the Neurokinin B analogs to block the scratching produced by substance P, Neurokinin B and bombesin, varying doses of the antagonists were injected simultaneously with that dose of agonist causing 90% of the animals to scratch. The ID$_{50}$ (that dose of antagonist which inhibits the scratching produced by an agonist by 50%) was then calculated by probit analysis. In some instances, the percent inhibitions of scratching for a given dose of agonist was compared to control values by the Fishers Exact Test. The following results were obtained in the Scratching Assay:

TABLE I

Antagonism of Substance P, Neurokinin B and Bombesin-Induced Scratching

| Product of | ID$_{50}$ vs. NK[a] | ID$_{50}$ vs SP[a] | % Inhibition of Bombesin[b] |
|---|---|---|---|
| Example 1 | 0.6 μg (0.3–1.2)[c] | 3.4 μg (2.3–5.2)[c] | 30% at 20 μg[b] |
| Example 2 | 80% at 10 μg[b] | 90% at 10 μg | 20% at 20 μg |
| Example 3 | 90% at 10 μg | 70% at 10 μg | 30% at 20 μg |
| Example 4 | 90% at 10 μg | 50% at 10 μg | 30% at 20 μg |
| [D-Pro$^2$, D-Trp$^{7,9}$]-SP$_{(1-11)}$ | 2.6 (0.8–4.8) | 4.6 (2.9–6.9) | 20% at 20 μg |

[a] an SD$_{90}$ dose (that dose which causes 90% of the animals to scratch) with NK or SP was used in combination with varying doses of antagonist to obtain the ID$_{50}$ values.
[b] % inhibition of scratching at specified dose.
[c] Value is the ID$_{50}$ (that dose of antagonist which inhibits NK or SP induced scratching by 50%) and values in parenthesis are 95% fiducial limits.

From the above Table I, it can be seen that all of the Neurokinin B analogs of the invention inhibited substance P- and Neurokinin B-induced scratching. At doses two times higher than those which blocked tachykinin-induced scratching, there was no significant block of bombesin-induced scratching. These data demonstrate that analogs are selective tachykinin antagonists. In particular, it has been demonstrated by G. Holmdahl and G. Bynke, supra, that Subtance P antagonists, like those of the present invention, are useful as anti-inflammatory agents in the eye.

Analgesic Utility

The Mouse Hot Plate Assay was used to determine the activity of compounds of the invention as analgesics. The compound vehicles were as described above in the Scratching Assay.

Mouse Hot Plate Assay

The hot plate assay was used to assess analgesic potency, see Vaught and Chipkin, Eur. Journal. Pharmacol. 79, 167–173 (1982) and references therein. In these experiments the hot plate apparatus (Technilab Instruments, Inc.) was maintained at 48±0.05° C. The response measure was the time interval between the animal being placed on the heated surface and licking or shaking its hindpaw. Test drug was administered intrathecally and at appropriate times following drug administration the reaction times redetermined. A reaction time for drug-treated animals greater than three standard deviations from the mean of the control reaction times for all the animals in the group was the criterion for an analgesic response. At least three doses with 10 animals per dose were used to construct dose response curves. A computer assisted probit analysis was used to generate ED$_{50}$ (that dose which produces analgesia in 50% of the animals) values and 95% fiducial limits.

The results obtained are shown in the following Table II:

TABLE II

Analgesic Effects of [D-Pro$^2$, D-Trp$^{7,9}$]-Substance P$_{(1-11)}$ and the Invention Neurokinin B Analogs

| Product of | ED$_{50}$ (μg)[a] | Onset of Action (min)[b] | Duration of Action (min)[c] |
|---|---|---|---|
| Example 1 | 4.6 (3.0–6.4) | 20 | ≧90 |
| Example 2 | 7.5 (5.9–9.5) | 20 | 120 |
| Example 3 | 10.4 (7.7–13.2) | 20 | ≦90 |
| Example 4 | 10.0 (5.5–18.2) | 20 | ≦60 |
| [D-Pro$^2$, D-Trp$^{7,9}$]-SP$_{(1-11)}$ | 5.5 (3.2–6.8) | 5 | ≦15 |

[a] Values represent the ED$_{50}$ and 95% fiducial limits.
[b] Time to peak analgesic activity following intrathecal injection of compound.
[c] Duration of the analgesic effect.

From the above Table II, it can be seen that following intrathecal administration to mice, all of the invention Neurokinin B analogs produced a dose-dependent analgesia. Of particular interest is the duration of action which was quite prolonged when compared to that produced by a substance P antagonist.

For the treatment of pain in humans, compounds of the present invention of formula (I) or salts thereof such as alkali earth, alkaline earth or organic salts such as dicyclohexylammonium, may be injected in vehicle into the spinal cord. As a vehicle, any standard artificial cerebrospinal fluid may be used. The dosage for analgesia would be about 1 to 50 micrograms of the compound of formula (I) for an average human.

The compounds of the present invention may be utilized as analgesic and/or anti-inflammatory agents in the mammalian eye by formulation with topical opthalmic vehicles, diluents, preservatives and other components used in liquid opthalmic pharmaceuticals. Standard opthalmic specifications include a saline solution, e.g. a 0.9 percent saline solution, a concentration of active compound of about $10^{-2}$ to $10^{-4}$ molarity, a benzalkonium chloride preservative, a buffer system of a mono- or di-phosphate to establish a pH of about 6.8 to 7.4, and methylcellulose or hydroxypropylmethylcellulose to help dissolve the active compound. Complexing the peptide of the invention, e.g. use of an ester derivative at one or both of the aspartic acid moieties may serve to increase its bioavailability. The opthalmic solution of the invention may be applied to the eye in a dose range of 1–4 drops, 1 to 4 times per day following trauma or insult to the eye to relieve pain and/or inflammation. In addition, standard injectable solutions may be utilized for the administration of one or more compounds according to the invention for the treatment of inflammation at a particular internal site, e.g. internally in the eye.

Also part of the present invention is a method for separation of a peptide, e.g. about 2 to 200 or 2 to 40 amino acids, on a HPLC column which is stable to basic media which comprises using as the solvent, an aqueous media containing piperidine, e.g. about 0.01 to 1% by volume piperidine. This has the advantage of being a volatile buffer which can be removed by lyophilization.

Throughout this specification, the following abbreviations may be used: Boc (t-butyloxycarbonyl); Asp (aspartic acid); Pro (proline); His (histidine); Phe (phenylalanine); Trp (tryptophan); Val (valine); Leu (leucine); Nle (norleucine); mg (milligrams); mmole (millimole); g (grams); μg (micrograms); min (minutes); hr (hours); ml (milliliters); M (molar); TFA (trifluoroacetic acid); HPLC (high pressure liquid chromatography); nm (nanometers); mm (millimeters); cm (centimeters); DMSO (dimethylsulfoxide); NK (neurokinin B); SP (substance P); and C, H, N, O etc. (the chemical sym-

What is claimed is:

1. A decapeptide of the following formula (I):

$$A^1\text{-D-Pro}^2\text{-His}^3\text{-D}^4\text{-Phe}^5\text{-D-Trp}^6\text{-Val}^7\text{-D-Trp}^8\text{-Leu}^9\text{-Nle}^{10}\text{-NH}_2$$

wherein
$A^1$ is $Asp^1$ or $D\text{-}Asp^1$; and
$D^4$ is $Asp^4$ or $D\text{-}Asp^4$,
and the pharmaceutically acceptable salts thereof, provided that if $A^1$ is $Asp^1$, $D^4$ is not $Asp^4$.

2. An opthalmic pharmaceutical composition comprising an analgesic or anti-inflammatory amount of a decapeptide of the following formula (I) in association with a pharmaceutically-acceptable vehicle:

$$A^1\text{-D-Pro}^2\text{-His}^3\text{-D}^4\text{-Phe}^5\text{-D-Trp}^6\text{-Val}^7\text{-D-Trp}^8\text{-Leu}^9\text{-Nle}^{10}\text{-NH}_2 \quad (I)$$

wherein
$A^1$ is $Asp^1$ or $D\text{-}Asp^1$; and
$D^4$ is $Asp^4$ or $D\text{-}Asp^4$,
and the pharmaceutically acceptable salts thereof.

3. A method for the treatment of pain or inflammation in the eye comprising administering thereto the opthalmic pharmaceutical composition of claim 2.

4. The method of claim 3 wherein said administration is topical.

5. The method of claim 3 wherein said administration is internal.

6. The pharmaceutical composition of claim 2, wherein said decapeptide of formula (I) is:

$$Asp^1\text{-D-Pro}^2\text{-His}^3\text{-Asp}^4\text{-Phe}^5\text{-D-Trp}^6\text{-Val}^7\text{-D-Trp}^8\text{-Leu}^9\text{-Nle}^{10}\text{-NH}_2.$$

7. The pharmaceutical composition of claim 2, wherein said decapeptide of formula (I) is:

$$D\text{-}Asp^1\text{-D-Pro}^2\text{-His}^3\text{-Asp}^4\text{-Phe}^5\text{-D-Trp}^6\text{-Val}^7\text{-D-Trp}^8\text{-Leu}^9\text{-Nle}^{10}\text{-NH}_2.$$

8. The pharmaceutical composition of claim 2, wherein said decapeptide of formula (I) is:

$$D\text{-}Asp^1\text{-D-Pro}^2\text{-His}^3\text{-D-Asp}^4\text{-Phe}^5\text{-D-Trp}^6\text{-Val}^7\text{-D-Trp}^8\text{-Leu}^9\text{-Nle}^{10}\text{-NH}_2.$$

9. The pharmaceutical composition of claim 2, wherein said decapeptide of formula (I) is:

$$Asp^1\text{-D-Pro}^2\text{-His}^3\text{-D-Asp}^4\text{-Phe}^5\text{-D-Trp}^6\text{-Val}^7\text{-D-Trp}^8\text{-Leu}^9\text{-Nle}^{10}\text{-NH}_2.$$

10. The pharmaceutical composition of claim 2, provided that if $A^1$ is $Asp^1$, $D^4$ is not $Asp^4$.

* * * * *